United States Patent
Zipper

(10) Patent No.: US 10,743,929 B2
(45) Date of Patent: *Aug. 18, 2020

(54) BULBOUS TIPPED SURGICAL DEVICE AND METHOD FOR DECREASING THE SIZE AND/OR CHANGING THE SHAPE OF PELVIC TISSUES

(76) Inventor: Ralph Zipper, Melbourne, FL (US)

( * ) Notice: Subject to any disclaimer, the term of this patent is extended or adjusted under 35 U.S.C. 154(b) by 1195 days.

This patent is subject to a terminal disclaimer.

(21) Appl. No.: 12/687,991

(22) Filed: Jan. 15, 2010

(65) Prior Publication Data
US 2011/0004202 A1 Jan. 6, 2011

Related U.S. Application Data

(63) Continuation-in-part of application No. 12/496,216, filed on Jul. 1, 2009, now Pat. No. 8,975,264.

(51) Int. Cl.
*A61B 18/24* (2006.01)
*A61B 18/14* (2006.01)
(Continued)

(52) U.S. Cl.
CPC .......... *A61B 18/1402* (2013.01); *A61B 18/24* (2013.01); *A61B 17/42* (2013.01); *A61B 18/1815* (2013.01); *A61B 2018/2005* (2013.01)

(58) Field of Classification Search
CPC . A61B 18/22; A61B 2018/208; A61C 1/0046; A61C 19/003; A61N 1/0524;
(Continued)

(56) References Cited

U.S. PATENT DOCUMENTS

| 4,862,886 A | 9/1989 | Clarke et al. |
| 5,207,672 A * | 5/1993 | Roth et al. ...................... 606/10 |

(Continued)

FOREIGN PATENT DOCUMENTS

| WO | WO9304727 | 3/1993 |
| WO | WO 2006/103678 | * 10/2006 |

OTHER PUBLICATIONS

Web page from napcore.com "What is PET?".*
(Continued)

*Primary Examiner* — Michael W Kahelin
*Assistant Examiner* — Shirley X Jian
(74) *Attorney, Agent, or Firm* — Stephen C. Thomas

(57) ABSTRACT

Low level laser energy may be delivered transmucosally to the vagina or other pelvic tissue. Such a device and its method of use may lead to healing of tissue, reduction of inflammation and pain, reduction in bladder problems such as urgency, frequency, and urinary incontinence, reshaping of tissue, and creation of a fertile environment for the potential implantation of stem cells. A probe may be moved in and out of the vagina in order to deliver the energy to the selected tissues. The probe may have a bulbous distal end that provides laser energy in a uniform 360 degree pattern or as close to 360 degrees of illumination as is structurally possible. Alternate embodiments may emit laser energy anywhere within the range from 0 degrees to 360 degrees. The scope of the present invention further includes the possibility of substituting alternate energy sources in place of laser energy.

16 Claims, 9 Drawing Sheets

(51) Int. Cl.
 *A61B 18/20* (2006.01)
 *A61B 18/18* (2006.01)
 *A61B 17/42* (2006.01)

(58) Field of Classification Search
 CPC .......... A61N 1/36007; A61N 2005/061; A61N 1/0611; A61N 1/063; A61N 1/0635; A61N 1/0643; A61N 1/0644; G02B 27/0905; G02B 27/0994; G02B 6/4204
 USPC .................. 909/7–18; 606/7–18; 607/88–90
 See application file for complete search history.

(56) References Cited

U.S. PATENT DOCUMENTS

| | | | |
|---|---|---|---|
| 5,219,343 A | 6/1993 | L'Esperance, Jr. | |
| 5,725,522 A | 3/1998 | Sinofsky | |
| 6,387,088 B1 | 5/2002 | Shattuck et al. | |
| 6,587,731 B1 | 7/2003 | Ingle et al. | |
| 6,607,525 B2 | 8/2003 | Franco | |
| 6,887,260 B1 * | 5/2005 | McDaniel | 606/9 |
| 7,931,028 B2 * | 4/2011 | Jay | A61N 5/0616 607/88 |
| 8,795,246 B2 * | 8/2014 | Hu | A61M 1/0066 604/319 |
| 2003/0065400 A1 | 4/2003 | Beam et al. | |
| 2003/0232303 A1 | 12/2003 | Black | |
| 2007/0082403 A1 | 4/2007 | Yang et al. | |
| 2007/0190544 A1 | 8/2007 | Giannakakou et al. | |
| 2008/0195087 A1 | 8/2008 | Wang et al. | |
| 2008/0201826 A1 | 8/2008 | Pryor et al. | |
| 2008/0262394 A1 | 10/2008 | Pryor et al. | |
| 2008/0306472 A1 | 12/2008 | Pryor et al. | |
| 2009/0012587 A1 | 1/2009 | Wang et al. | |
| 2009/0082759 A1 | 3/2009 | Pryor et al. | |
| 2009/0153837 A1 | 6/2009 | Wang et al. | |
| 2009/0299236 A1 | 12/2009 | Pryor et al. | |
| 2009/0319008 A1 * | 12/2009 | Mayer | A61N 5/0603 607/90 |
| 2010/0241038 A1 | 9/2010 | Pryor et al. | |
| 2010/0256541 A1 | 10/2010 | Pryor et al. | |
| 2010/0286576 A1 * | 11/2010 | Pryor | A61H 21/00 607/88 |
| 2011/0000420 A1 | 1/2011 | Vaught | |
| 2011/0004202 A1 | 1/2011 | Zipper | |
| 2011/0004203 A1 | 1/2011 | Zipper | |
| 2011/0009852 A1 | 1/2011 | Pryor et al. | |
| 2011/0020173 A1 | 1/2011 | Pryor et al. | |
| 2011/0144724 A1 | 6/2011 | Pryor et al. | |
| 2011/0144725 A1 | 6/2011 | Pryor et al. | |
| 2011/0144726 A1 | 6/2011 | Pryor et al. | |
| 2011/0224584 A1 * | 9/2011 | Pryor | A61H 21/00 601/15 |

OTHER PUBLICATIONS

Office Action on U.S. Appl. No. 12/687,965 dated Mar. 13, 2013 for applicant Ralph Zipper.
Office Action on U.S. Appl. No. 12/496,216 dated Oct. 23, 2012 for applicant Ralph Zipper.

* cited by examiner

ENDOPELVIC FASCIA

BULBOUS TIPPED SURGICAL DEVICE AND METHOD FOR DECREASING THE SIZE AND/OR CHANGING THE SHAPE OF PELVIC TISSUES

CROSS REFERENCE TO RELATED APPLICATIONS

This application is a continuation-in-part of Ser. No. 12/496,216, filed with the USPTO on Jul. 1, 2009, U.S. Pat. No. 8,795,264 which is herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The present invention generally relates to surgical methods, more specifically, the present invention relates to changing the shape and/or size of tissues and structures within the pelvic region including but not limited to the vagina, labia, prepuce, perineum, and other supportive tissues.

2. Background Art

Many women are unhappy with the size, shape, and/or contour of the vagina or labia. This may be secondary to changes that occur with childbirth, vaginal or pelvic surgery, and/or aging. Sometimes the size, shape, and/or contour abnormality may be congenital. This enlargement and/or unsatisfactory shape or contour may lead to sexual dysfunction which may be anatomic or psychological in nature. Until recently, vaginal reconstruction and vulvar surgery has been reserved for the treatment of neoplasia and prolapse. As women have become more outspoken about their dissatisfaction with their genitalia, surgeons have begun to offer those patients surgical corrections typically utilized for the treatment of neoplasia and prolapse. Although these surgeries may alter the size and shape of the vagina and labia, they may often compromise sexual function or create less than optimal aesthetic results.

Presently utilized surgeries injure tissue, deform anatomy, or remove vital tissue. The sexual dysfunction created by such surgeries may be secondary to stenosis of the vagina, shortening of the vagina, injury to muscles or nerves leading to pain or anesthesia, injury of the Graffenberg Spot, removal of the Graffenberg spot, or poor aesthetic appearance leading to psychological sexual dysfunction.

Injuries to the supporting structures of the vagina and surrounding tissues may also cause urinary incontinence. Present treatments for urinary incontinence do not restore normal anatomic structure. Such treatments either create new support with donor or synthetic tissue or distort anatomy to create a compensatory mechanism for managing the defect.

BRIEF SUMMARY OF THE INVENTION

In accordance with one embodiment, a method for treating frequency of urination, urgency of urination, urge incontinence, pelvic pain, pain with intercourse, or reshaping pelvic tissue via transmucosal energy delivery, the method comprising the steps of providing a probe capable of emitting an energy source from a bulbous distal end of the probe wherein the bulbous distal end is translucent and emits the energy source in a three dimensional field defined by an angular range from 0 degrees to 360 degrees, inserting the probe into the pelvic tissue, activating the energy source, and translating the distal end of the probe across the pelvic tissue.

In accordance with another embodiment of the present invention, a device for treating frequency of urination, urgency of urination, urge incontinence, pelvic pain, pain with intercourse, or reshaping pelvic tissue, the device comprising a laser fiber, the laser fiber having a proximal end capable of attachment to a laser energy source and a distal end capable of emitting laser energy, a probe body disposed about at least a distal portion of the laser fiber, and a bulbous distal tip connected to the distal end of the probe body, wherein the bulbous distal tip is translucent and emits the laser energy in a three dimensional field defined by an angular range from 0 degrees to 360 degrees.

DETAILED DESCRIPTION OF THE INVENTION

The scope and breadth of the present inventive disclosure is applicable across a wide variety of procedures, tissues and anatomical structures. Although the following detailed description contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention.

Figure 1A:
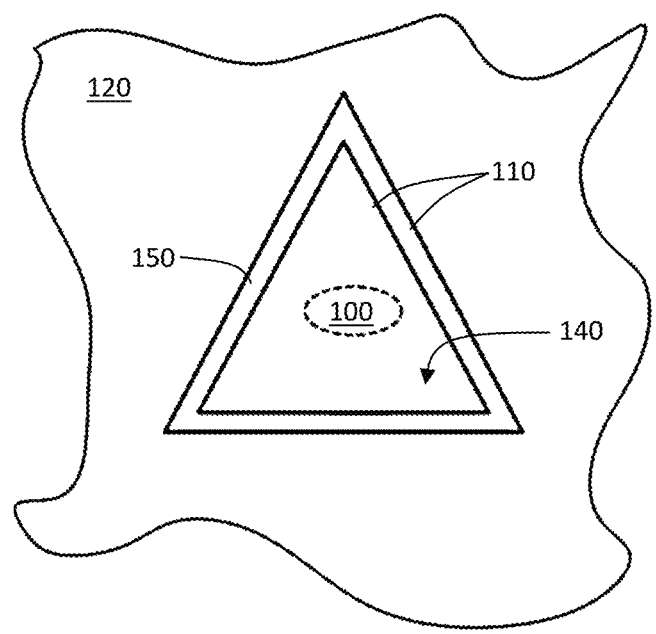
FIG. 1A depicts a schematic diagram of one step in a first embodiment of the present invention.
Figure 1B:
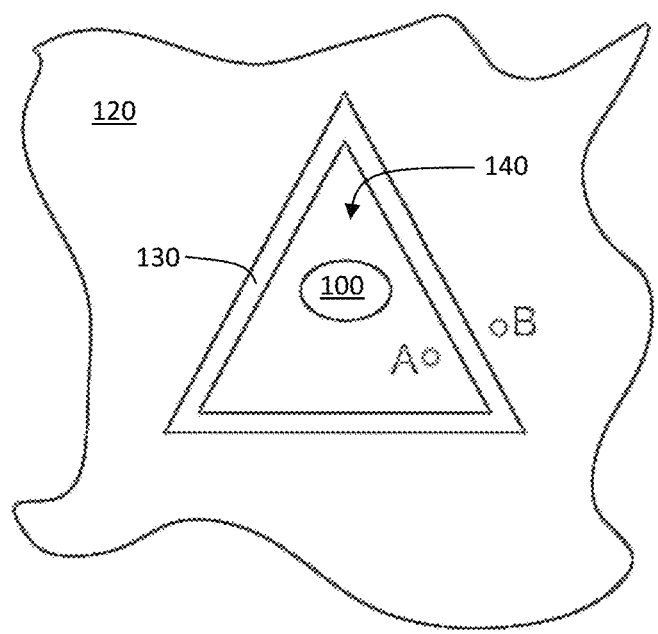
FIG. 1B depicts a schematic diagram of another step in the first embodiment of the present invention.
Figure 1C:
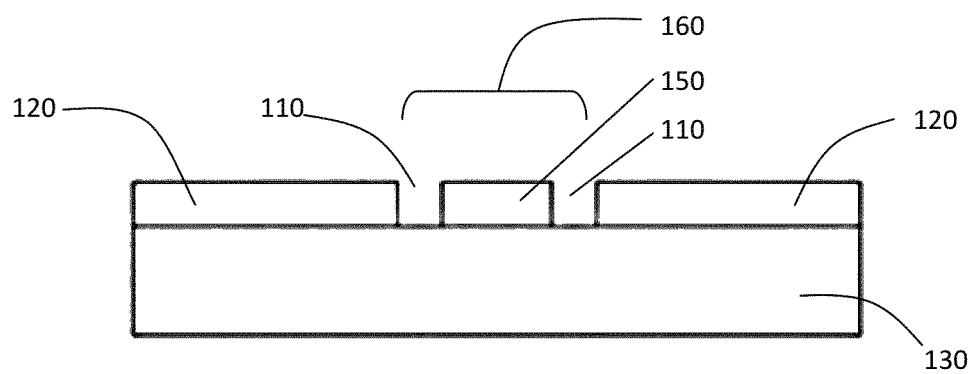
FIG. 1C depicts a schematic diagram of still another step in the first embodiment of the present invention.
Figure 1D:
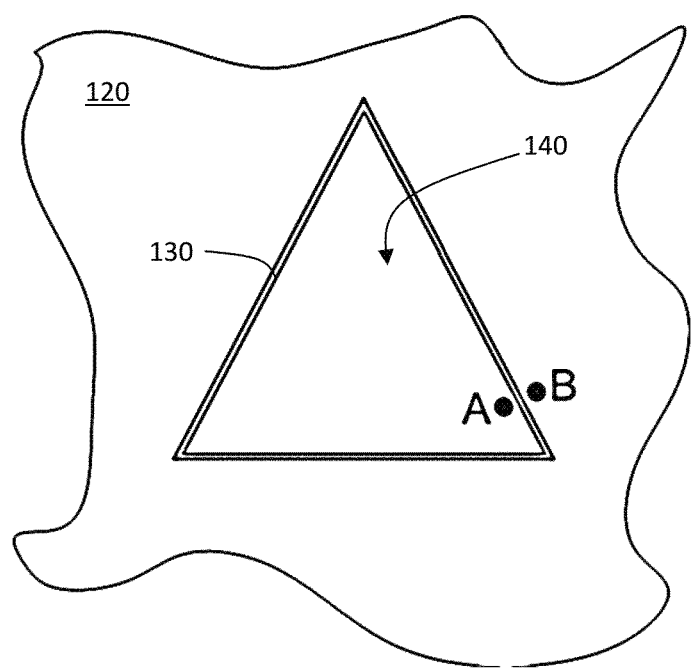
FIG. 1D depicts a schematic diagram of yet another step in the first embodiment of the present invention.

A first embodiment, depicted in FIGS. 1A-1D, may provide for protection of the Graffenberg Spot (G-Spot). In this embodiment, the vaginal mucosa of the G-Spot 100 may be left intact. At least one incision 110 of any known shape, preferably triangular-shaped, may be made around the G-Spot 100, as shown in FIG. 1A. The at least one incision 110 may be carried through the thickness of the vaginal mucosa 120. The at least one incision 110 may spare the endopelvic fascia 130. A preferably triangular-shaped island 140 of mucosa 120 may then be created. A strip 150 of mucosa 120 may be removed from the circumference of the island 140 to expose a channel 160 of endopelvic fascia 130, as shown in FIG. 1B and FIG. 1C. The diameter of this channel 160 will determine the final shape and/or size of the vagina. As shown in FIG. 1D, radio frequency (RF) energy may then be applied to shrink the channel 160 of endopelvic fascia 130 and close the gap between the mucosal 120 edges as shown by the relative movement of point A and point B. The limited penetration of RF energy spares the underlying nerve structure and improves the thickness of peri-island fascia. The mucosal 120 edges may be left "as is", approximated with sutures or glue, or closed by any other manner known within the art. Although RF is the preferred energy source, any other types of energy known within the art including but not limited to laser, microwave, and monopolar or bipolar electrosurgery may be used.

Figure 2A:
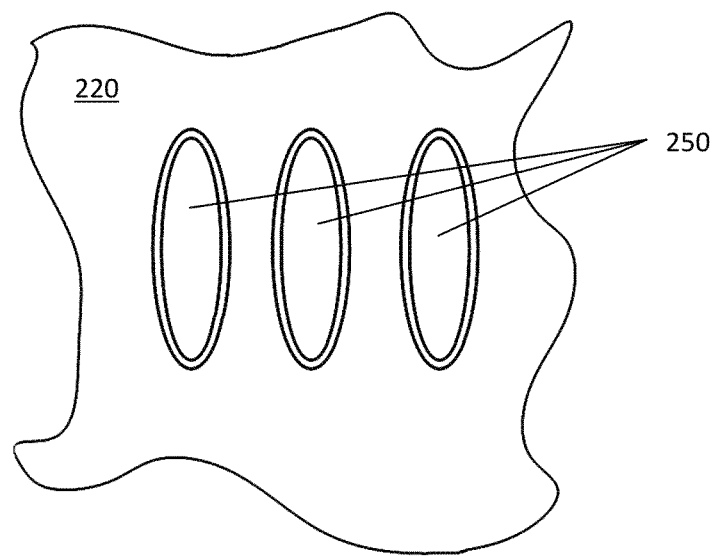
FIG. 2A depicts a schematic diagram of one step in a second embodiment of the present invention.
Figure 2B:
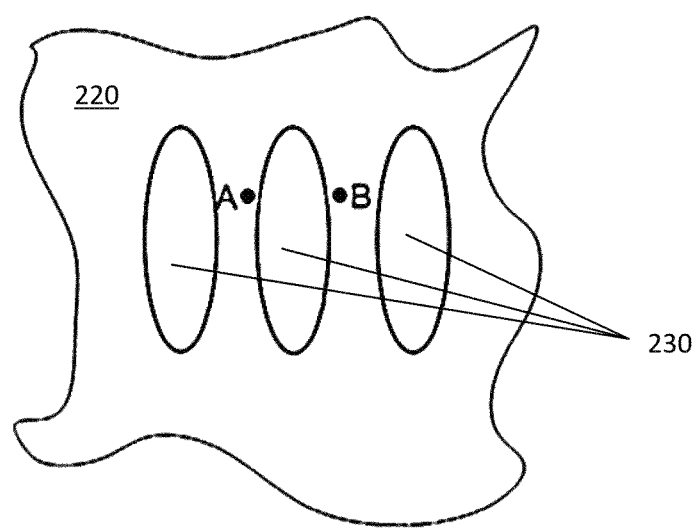
FIG. 2B depicts a schematic diagram of another step in the second embodiment of the present invention.
Figure 2C:
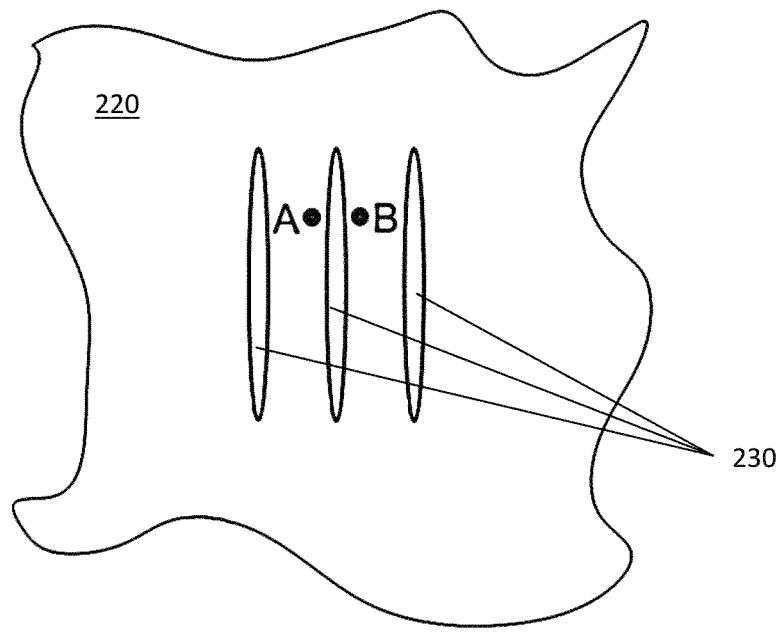
FIG. 2C depicts a schematic diagram of still another step in the second embodiment of the present invention.

A second embodiment, depicted in FIGS. 2A-2C, may provide for vaginal shaping without removal of fascia. In this embodiment, as shown in FIG. 2A, strips 250 of vaginal mucosa 220 may be removed while sparing the underlying endopelvic fascia 230 and nerve injury (see FIG. 2B). Rather than pulling the mucosal 220 edges together and creating a submucosal deformity, RF energy may be applied to shrink the endopelvic fascia 230 and bring the mucosal 220 edges closer together, as shown by the relative movement of point A and point B in FIGS. 2B and 2C. The limited penetration of RF energy acts to spare the underlying nerve structure and improves the thickness of underlying tissue. The mucosal 220 edges may be left "as is", approximated with sutures or glue, or closed by any other manner known within the art. Although RF is the preferred energy source, any other types of energy known within the art including but not limited to laser, microwave, and monopolar or bipolar electrosurgery may be used.

Figure 3A:
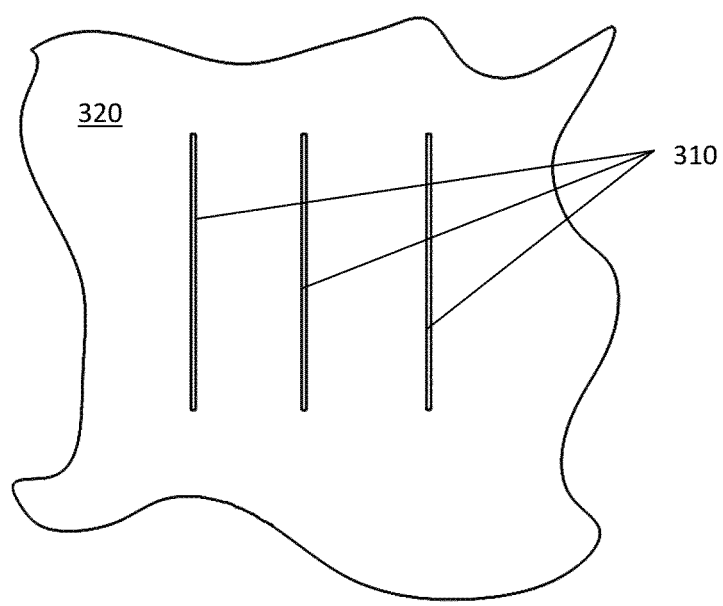
FIG. 3A depicts a schematic diagram of one step in a third embodiment of the present invention.
Figure 3B:
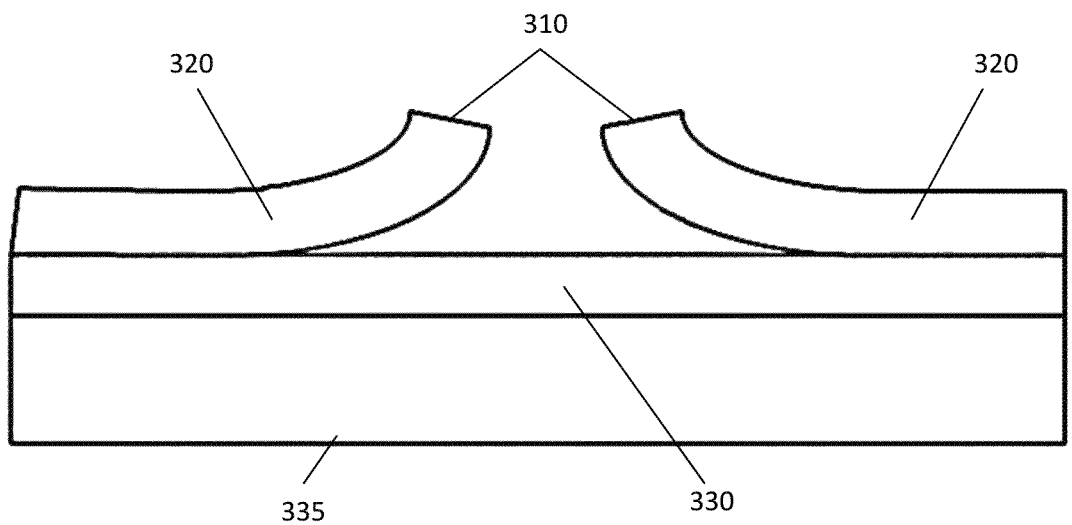
FIG. 3B depicts a schematic diagram of another step in the third embodiment of the present invention.
Figure 3C:
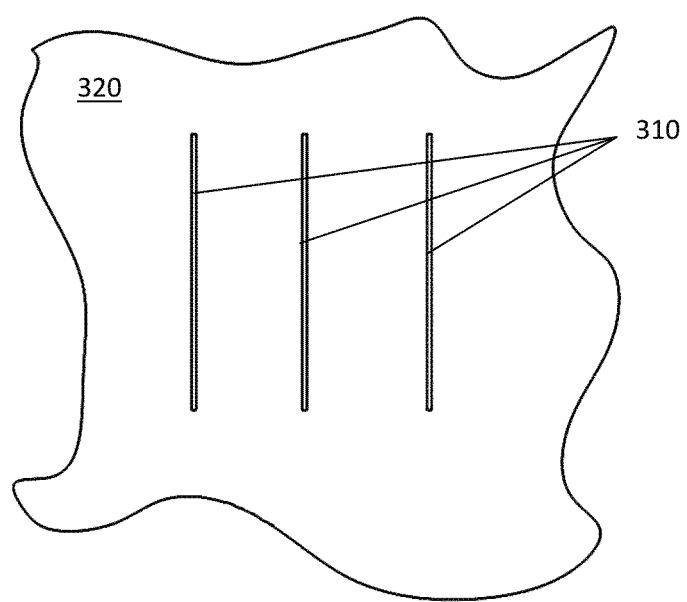
FIG. 3C depicts a schematic diagram of still another step in the third embodiment of the present invention.

A third embodiment, depicted in FIG. 3A-3C, may provide for vaginal shaping without removal of mucosa. As shown in FIG. 3A, one or more incisions 310 may be made in the mucosa 320. The endopelvic fascia 330 or other submucosal tissue may be left attached to the mucosa 320. As shown in FIG. 3B, RF energy may be applied to the endopelvic fascia 330 or other submucosal tissue exposed between the incision 310 margins. Such an application of energy will cause shrinkage of such endopelvic fascia 330 tissue with proportional contraction of the overlying mucosa 320 and spare the deep nerves and subfascial or subcutaneous tissue 335. Any such endopelvic fascia 330 that is left exposed (as expressly disclosed in all embodiments) may be treated with RF energy. In this manner, the mucosal 320 edges closer together and provide a new contour or shape to the mucosa 320, as shown in FIG. 3C. The mucosal 320 edges may be left "as is", approximated with sutures or glue, or closed by any other manner known within the art. Although RF is the preferred energy source, any other types of energy known within the art including but not limited to laser, microwave, and monopolar or bipolar electrosurgery may be used.

A fourth embodiment may provide for contouring of the prepuce. As expressly disclosed in the method steps above, an incision may be created around the prepuce and RF energy may thereafter be applied to the underlying fascia. Such an embodiment is similar to that shown in FIGS. 3A-3C and analogous steps may be applied to the prepuce. Although RF is the preferred energy source, any other types of energy known within the art including but not limited to laser, microwave, and monopolar or bipolar electrosurgery may be used.

A fifth embodiment may provide for contouring of the labia minora. As expressly disclosed in the method steps above, an incision may be made in the labia minora. The subcutaneous tissue may not be separated from the epithelium. RF energy may then be applied to the subcutaneous tissue. The shrinkage of the subcutaneous tissue and/or fascia shall contour the labia. Such an embodiment is similar to that shown in FIGS. 3A-3C and analogous steps may be applied to the labia minora. Although RF is the preferred energy source, any other types of energy known within the art including but not limited to laser, microwave, and monopolar or bipolar electrosurgery may be used.

A sixth embodiment may provide for contouring of the perineum. As expressly disclosed in the method steps above, a portion of perineum skin may be removed sparing the underlying fascia and nerves. RF energy may then be applied to the fascia and other subcutaneous tissue. The shrinkage of the subcutaneous tissue and/or fascia will bring the epithelial edges closer together. The edges may be left "as is", approximated with sutures or glue, or closed by any other manner known within the art. Such an embodiment is similar to that shown in FIGS. 2A-2C and analogous steps may be applied to the perineum. Although RF is the preferred energy source, any other types of energy known within the art including but not limited to laser, microwave, and monopolar or bipolar electrosurgery may be used.

A seventh embodiment may provide for contouring of the labia majora. As expressly disclosed in the method steps above, an incision may be made in the labia majora. The subcutaneous tissue may not be separated from the epithelium. RF energy may then be applied to the subcutaneous tissue. The shrinkage of the subcutaneous tissue and/or fascia shall contour the labia. Such an embodiment is similar to that shown in FIGS. 3A-3C and analogous steps may be applied to the labia majora. Although RF is the preferred energy source, any other types of energy known within the art including but not limited to laser, microwave, and monopolar or bipolar electrosurgery may be used.

As an alternative or addition, a portion of labial skin may be removed sparing the underlying fascia and nerves. RF energy may then be applied to the subcutaneous tissue and/or fascia. The shrinkage of the subcutaneous tissue and/or fascia will bring the labial skin edges closer together. The edges may be left "as is", approximated with sutures or glue, or closed by any other manner known within the art. Such an embodiment is similar to that shown in FIGS. 2A-2C and analogous steps may be applied to the labial skin. Although RF is the preferred energy source, any other types of energy known within the art including but not limited to laser, microwave, and monopolar or bipolar electrosurgery may be used.

Figure 4A:
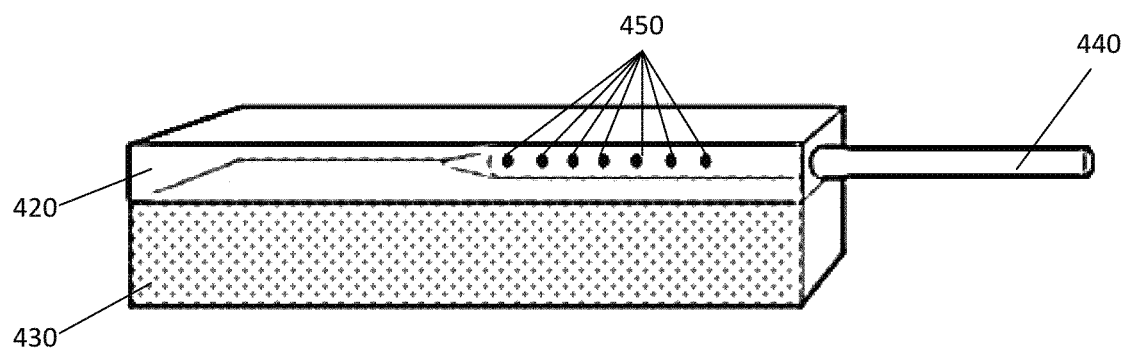
FIG. 4A depicts a schematic diagram of a treatment phase of a fourth embodiment of the present invention.
Figure 4B:
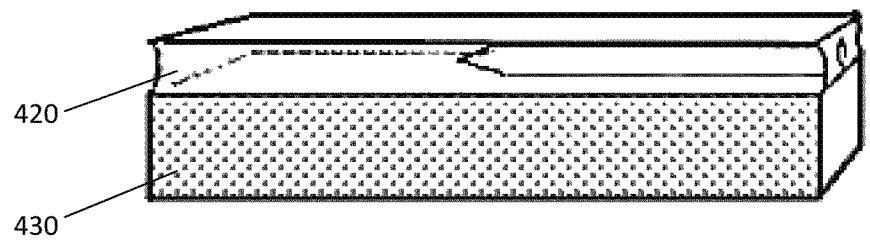
FIG. 4B depicts a schematic diagram of a post-treatment phase of the fourth embodiment of the present invention.

An eighth embodiment, depicted in FIG. 4A and FIG. 4B, may provide for transmucosal and transcutaneous contouring. As shown in FIG. 4A, pelvic tissues including but not limited to the vaginal mucosa, labia, prepuce, and/or perineum may be treated by the transcutaneous application of RF energy. In such an embodiment, RF energy may be applied to the tissue 430 (e.g. dermis, subcutaneous tissue, and/or fascia) below the mucosa or skin 420 without an incision being made or portions of the mucosa or skin 420 being removed. Application of such RF energy may preferably be via a needle, probe, or any other non-invasive instrument 440 known within the art. FIG. 4A depicts one embodiment performing the step of application of energy from one or more side ports 450 of a non-invasive means 440. As shown in FIG. 4B, the resultant shrinkage and changes to underlying tissue 430 shall shape the overlying structures as needed. Although RF is the preferred energy source, any other types of energy known within the art including but not limited to laser, microwave, and monopolar or bipolar electrosurgery may be used.

Figure 5A:
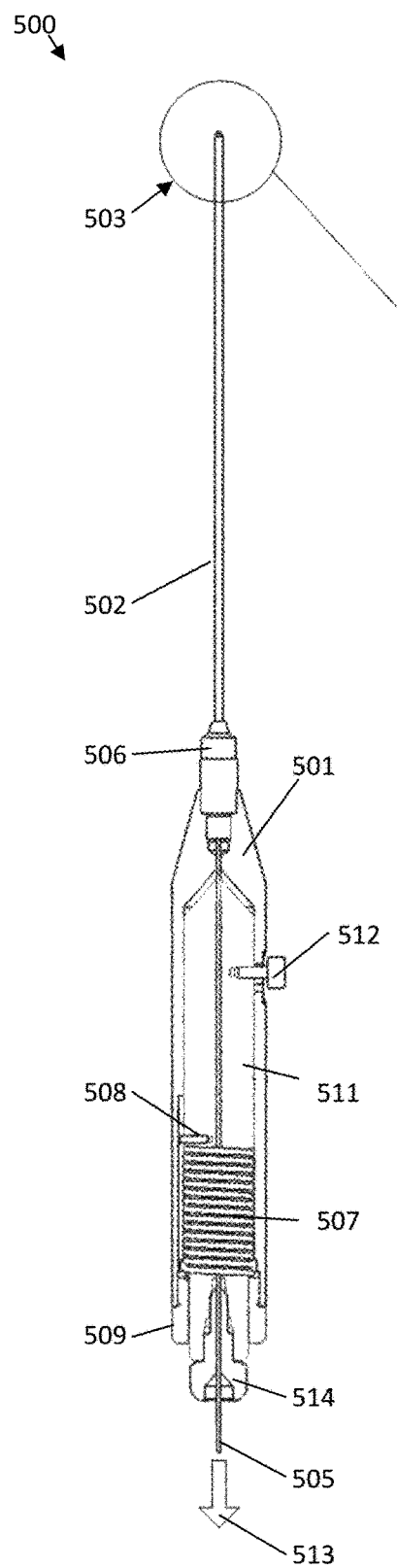
FIG. 5A depicts a side view of an embodiment of a laser energy source of the present invention.
Figure 5B:
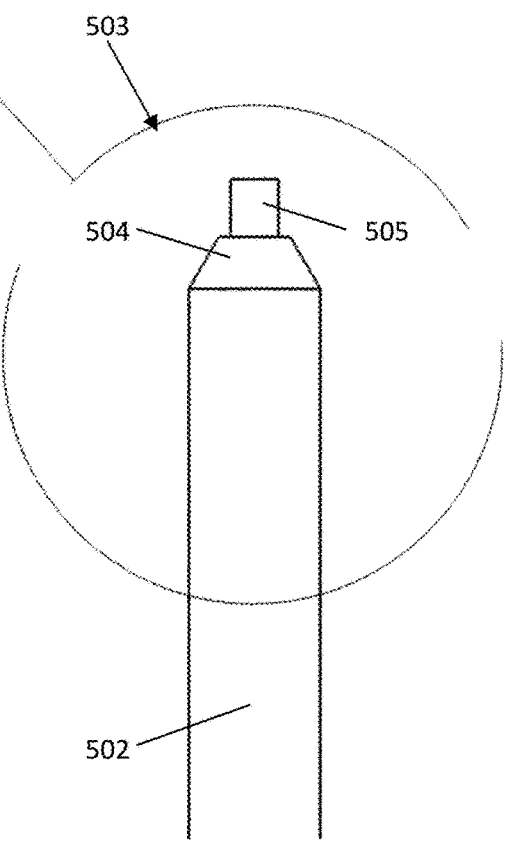
FIG. 5B depicts a magnified side view of the embodiment of the laser energy source of the present invention depicted in FIG. 5A.

Another effective embodiment, similar to that shown in FIGS. 4A and 4B, may involve the use of a cannula and laser fiber. FIG. 5A depicts one potential and preferred embodiment of such a cannula and laser fiber device 500. In one embodiment, the device 500 may comprise an outer housing 501 secured to a cannula 502 having a distal portion 503. The distal portion 503 may comprise a distal tip 504 from which a laser fiber 505 may be extended and retracted. FIG. 5B illustrates a close-up view of the laser fiber 505 disposed in an extended state and protruding beyond the distal tip 504 of the cannula 502. The device 500 may comprise additional optional features to facilitate use, such optional features may include but are not limited to male/female Luer locks 506 for attaching the cannula to the outer housing 501, and a compression spring 507, clocking pin 508, spring cap 509, slide body 511, and slide limiter 512 providing for modes of extending and retracting the laser fiber 505. The slide limiter 512 may be in communication with the laser fiber 505 and be used to manually advance or motivate the laser fiber 505 between the retracted position and the extended position during a procedure. The slide limiter 512 may comprise a button, knob, finger rest surface, and the like that are well known for motivating movable components of surgical devices within the art. The laser fiber 505 may extend from the proximal end of the device 500 to a laser source 513 through a fiber locking screw 514.

Initially, the laser fiber 505 may be advanced to the distal portion 503 of the cannula 502 and thereafter the cannula 502 may be inserted through a small puncture or bodily cavity and then advanced to the desired treatment area. The cannula 502 may then be slightly retracted and/or the laser fiber 505 advanced disposing the distal end of the laser fiber 505 just beyond the distal tip 504 of the cannula 502. The laser fiber 505 may then be activated to deliver energy along the pathway of the cannula's 502 withdrawal. This delivery of energy may be supplied either continuously or in a pulsed manner. The energy being delivered through the distal end of the laser fiber 505 may be altered in power, pulse width, and/or rest time in order to provide differential treatment along the path of the device 500. Application of energy in this manner will result in a shaping or molding of the tissue rather than a uniform contraction. One example of use of such a device 500 and/or method may be in the vagina where application of a greater energy distally will help to create the normal taper of the vagina. In a preferred embodiment, energy may be applied in the form of 980 nm-1064 nm wavelength laser to be effective. However, other laser wavelengths and other forms of energy may replace the 980 nm laser. In a preferred embodiment, 810-1064 nm will be delivered at no less than 4 watts and no more than 25 watts. In the preferred embodiment pulse time will be no less than 0.1 second and no more than 2.5 seconds of continuous energy. However, in circumstances where the cannula 502 is kept in continuous motion (pulled out without stopping), the pulse may be equal to the length of time required to treat the entire cannula removal or insertion tract with the cannula 502 moving no slower than 0.25 cm per second. The preferred total energy delivered to a single side of the vagina (anterior or posterior) is between 1000 joules and 4000 joules. In one variation of the preferred embodiment, the energy will be increased or decreased as the laser fiber 505 distal end approaches the opening of the vagina. If the vagina needs more tightening near the opening, the energy will be increased. If the apex of the vagina needs more shrinking than the opening of the vagina, the energy will be decreased as the laser fiber 505 distal end approaches the vaginal opening. The scope of the present invention includes the delivery of a constant power level, a continually or intermittently increasing power level, and/or a continually or intermittently decreasing power level during withdrawal of the cannula needle 502.

Preferably these power and/or pulse adjustments may be preset in the laser device 500. In one embodiment the laser power and/or pulse width will be serially increased or decreased each time the surgeon deactivates and then reactivates the laser (e.g. releases and steps back down on the laser pedal). Four typical presets start with the laser power at 12, 14, 17, and 19 watts and increase by 1 watt each time the surgeon reactivates the laser. The maximum increase is typically set between 5 and 10 watts. Once the maximum is reached, there may be no change in power with subsequent activations.

In another embodiment, the laser may be programmed to time out or deactivate once a predetermined maximum activation time, a predetermined maximum temperature, and/or a predetermined maximum energy level has been reached. Such maximum times, temperatures, or energies may be preset in the laser device 500 or be predetermined by user input using mechanical or digital input devices or method that are abundantly common and well known in the art such as knobs, buttons, touch screens, digital displays, and the like. In an activation time-dependent embodiment, the laser device 500 may deactivate or time out after a maximum activation time is reached, wherein the maximum activation time may be in the range between 0.01 seconds and 5.00 seconds. In a preferred embodiment, the maximum activation time is 2.5 seconds. In a temperature-dependent embodiment, the laser device 500 may deactivate or time out after a maximum temperature is reached, wherein the maximum temperature near the tip of the cannula 502 may be in the range between 60 degrees Celsius and 99 degrees Celsius. In an energy-dependent embodiment, the laser device 500 may deactivate or time out after a maximum energy level is reached. A preferred maximum energy level is in the range from 25 joules to 60 joules. After the laser device 500 has timed out or become deactivated after reaching the maximum time, temperature, or energy level, the laser device 500 may be reactivated by the surgeon. In one embodiment, the surgeon or other user may reactivate the laser device 500 by merely releasing and then again pressing the activation switch or pedal controlling the laser power of the device 500. Additionally, while the disclosure describes a preferred method of energy application during withdrawal of the device 500, energy may also be applied or delivered during advancement of the device 500 as well. Although the present embodiment utilizes a laser as the preferred energy source, any other types of energy known within the art including but not limited to RF, microwave, and monopolar or bipolar electrosurgery may be used with such respective structures replacing the laser fiber 505.

In a preferred embodiment of the device 500, forward pressure or advancement of the cannula 502 may cause the laser fiber 505 to move back against a spring 507. Similarly, backward movement or withdrawal of the cannula 502 may cause the laser fiber 505 to be advanced or extended beyond the distal tip 504 of the cannula 502 by the biasing force of the spring 507. In an alternate embodiment of the device 500, the laser fiber 505 may require manual advancement against the biasing force of a spring 507 to advance or extend the distal end of the laser fiber 505 beyond the distal tip 504 of the cannula 502.

Figure 6A:
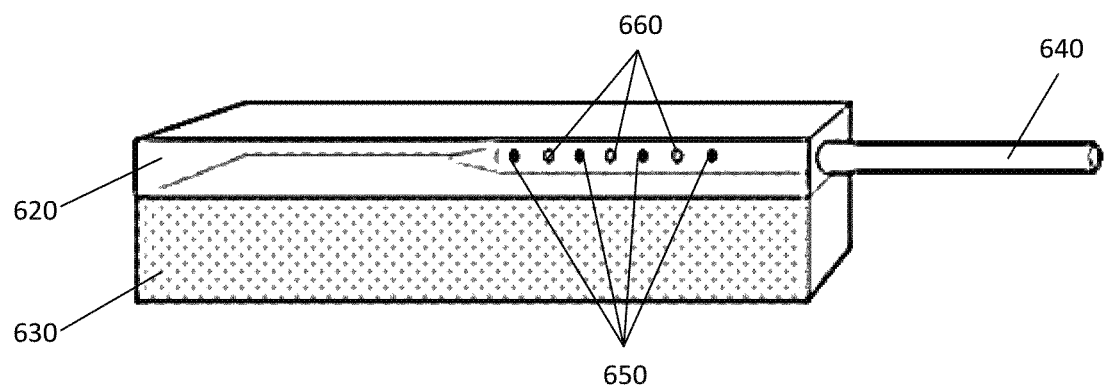
FIG. 6A depicts a schematic diagram of a treatment phase of a fifth embodiment of the present invention.
Figure 6B:
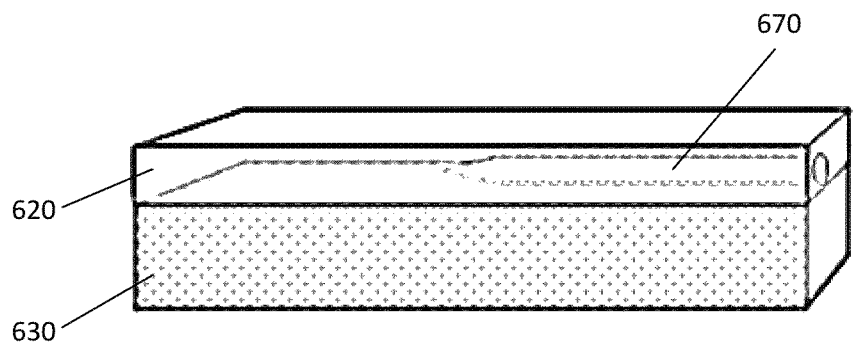
FIG. 6B depicts a schematic diagram of a post-treatment phase of the fifth embodiment of the present invention.

A ninth embodiment, depicted in FIG. 6A and FIG. 6B, may provide for applying minimally destructive energy directly or indirectly to the tissues 620 of the vagina and/or vulva, which may be followed by the implantation of stem cells 670. Such a "pretreatment" of energy may take the form of RF, microwave, laser, monopolar or bipolar electrosurgery, or any other surgical energy sources known within the art. As shown in FIG. 6A, the application of such energy may be delivered with or without an incision. Application of such RF energy may preferably be via a needle, probe, or any other non-invasive means 640 known within the art having application elements 650 such as ports, conduits, fibers, and the like respective to the specific type of energy source used. The pretreatment of energy creates an environment favorable to stem cells 670. Chemical pretreatment, via any known chemical agent(s), may also provide for minimal destruction and/or minimal injury. As shown in FIG. 6B, following pretreatment with an energy source the stem cells 670 may be implanted (i.e. treatment) through exit ports 660. Such implantation may be performed with a needle, via an incision, or any other means known within the art. The respective steps of pretreatment and treatment may be performed in either one stage or two separate stages and by one device or two separate devices.

A tenth embodiment may provide for a method of treating periurethral tissue. All method steps disclosed herein for decreasing the size or changing the shape of anatomical tissue, most particularly the ninth embodiment, may further be used in the treatment of periurethral tissue. Such treatments may improve the symptoms commonly associated with urinary incontinence.

Figure 7:
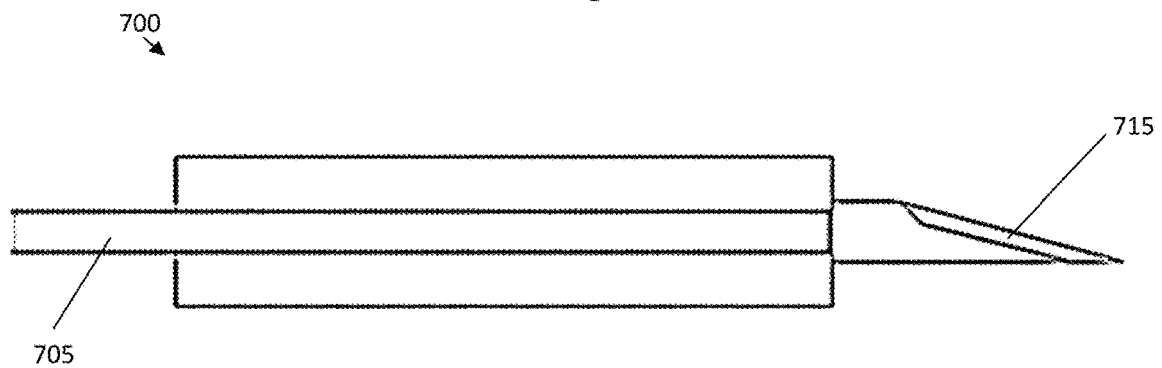
FIG. 7 depicts a side view of another embodiment of a laser energy source of the present invention comprising a laser scalpel.

In an eleventh embodiment, the shaping or resizing of the vulva or other pelvic structure may be facilitated by the delivery of energy through a mechanical cutting instrument. One embodiment of such a device is depicted in FIG. 7 and may consist of a glass scalpel 700 or any other similar instrument known within the art. Such a glass scalpel 700 or equivalent device may be used to simultaneously create a mechanical cut or incision and deliver laser energy for coagulation and tissue treatment (e.g. shrinkage) purposes. In a preferred embodiment, $CO_2$ laser energy may be delivered by a laser fiber 705 to the scalpel cutting blade 715 in the range of 2 watts to 15 watts of continuous power. The energy shall be delivered to the blade as close to $TEM_{00}$ as possible.

Figure 8:
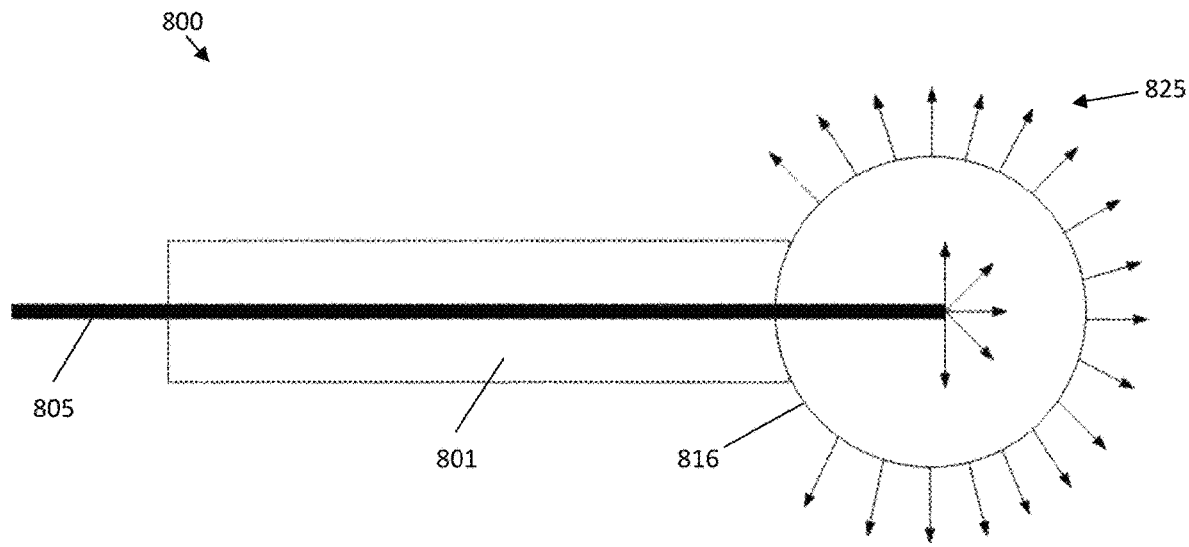
FIG. 8 depicts a side view of another embodiment of a laser energy source of the present invention.

In a twelfth embodiment as generally depicted in FIG. 8, low level laser energy may be delivered transmucosally to the vagina or other pelvic tissue. The use of such energy has been shown to increase cytochrome c oxidase production and reverse the effects of cellular inhibitors of respiration. Such steps may lead to healing of tissue, reduction of inflammation and pain, reduction in bladder problems such as urgency, frequency, and urinary incontinence, reshaping of tissue, and creation of a fertile environment for the potential implantation of stem cells.

In one embodiment, the low level laser energy may be delivered via a device 800 comprising a laser fiber 805 disposed inside a vaginal probe 801. The probe 801 may be moved in and out of the vagina in order to deliver the energy to the appropriate tissues. Multiple treatments may be necessary to achieve the desired effect. The probe 801 may be made of glass, plastic, any translucent material, any transparent material, or any other material known within the art and may have a bulbous or "roller ball" type distal end 816. Such a bulbous distal end 816 structure may allow for the bulb to be illuminated 825 and provide laser energy in a uniform 360 degree pattern about the distal end 816 or as close to 360 degrees of illumination as is structurally possible. Alternate embodiments may include distal ends 816 that emit laser energy in the range between 1 degree to 360 degrees. Exemplary embodiments may provide for a distal end 816 that emits laser energy (or an alternate energy) over a range of 45 degrees, 90 degrees, 180 degrees, 270 degrees, 360 degrees, or any increments there between.

While 980 nm and 808 nm wavelength lasers are the preferred energy sources, lasers having other wavelengths are also well within the scope of the present invention and include but are not limited to lasers having wavelengths in the range between 700 nm and 1200 nm. In another preferred embodiment, the energy source may provide laser energy having a wavelength of 810 nm, a wavelength of 980 nm, or the laser energy may provide distinct wavelengths of both 810 nm and 980 nm. The scope of the present invention also further includes the possibility of substituting laser energy with another energy source that may including but is not limited to RF energy, microwave energy, and monopolar or bipolar electrosurgical energy, and any combinations thereof.

In one method of use, the probe 801 may be inserted into the vagina until the distal end 816 reaches the vaginal apex. The laser fiber 805 may be in standby mode until the distal end 816 of the probe 801 is introduced into the vagina. Once the distal end 816 reaches the apex of the vagina, the laser fiber 805 may be put in ready mode. Once in ready mode, the laser 805 may be activated by stepping on a foot pedal. The user may step on the foot pedal once the distal tip 816 reaches the vaginal apex and then stay on the foot pedal while moving the probe 801 and distal end 816 in an "in and out" motion. In one embodiment, the probe 801 may be kept in constant motion for 3 to 10 minutes and may reach a total energy output of 500 joules to 6000 joules. In an alternate embodiment, the probe 801 may be translated using intermittent motion for 3 to 10 minutes and may reach a total energy output of 500 joules to 6000 joules. The preferred energy output range is 2000 joules to 4000 joules. The user may then release the foot pedal prior to the removal of the probe 801 and distal end 816 to place the laser 805 back in standby mode prior to extraction of the device 800.

While the above description contains much specificity, these should not be construed as limitations on the scope of any embodiment, but as exemplifications of the presently preferred embodiments thereof. Many other ramifications and variations are possible within the teachings of the various embodiments.

Thus the scope of the invention should be determined by the appended claims and their legal equivalents, and not by the specific examples given.

What is claimed is:

1. A method for treating frequency of urination, urgency of urination, urge incontinence, pelvic pain, pain with intercourse, or reshaping pelvic tissue via transmucosal energy delivery, said method comprising the steps of:
    providing a probe capable of emitting laser energy from a spherical distal end of said probe wherein said probe comprises a laser fiber disposed therein, and wherein said probe is fabricated from plastic or glass, is translucent, and emits said laser energy simultaneously in a spherical three dimensional field defined by an angular range from 45 degrees to 360 degrees from said spherical distal end;
    inserting said probe into said pelvic tissue until said probe reaches the vaginal apex;
    activating said energy source and transmitting said laser energy through said spherical distal end of said probe in said spherical three dimensional field such that said pelvic tissue is irradiated with laser energy transmucosally via said spherical three dimensional field; and
    translating said distal end of said probe across said pelvic tissue in a continuous in and out motion while said pelvic tissue is being irradiated, increasing the production of cytochrome c oxidase production in said pelvic tissue.

2. The method of claim 1, further comprising the steps of:
    deactivating said energy source; and
    removing said distal end of said probe from said pelvic tissue.

3. The method of claim 1, wherein said continuous motion is maintained for a period of time comprising three minutes to ten minutes in duration.

4. The method of claim 1, wherein said energy source is laser energy.

5. The method of claim 4, wherein said energy source comprises laser energy providing a wavelength in the range from 700 nm to 1200 nm.

6. The method of claim 5, wherein said energy source comprises laser energy providing a wavelength in the range from 808 nm to 980 nm.

7. The method of claim 1, wherein said energy source comprises laser energy comprising two distinct wavelengths.

8. The method of claim 7, wherein said two distinct wavelengths comprise 810 nm and 980 nm.

9. The method of claim 1, wherein said step of translating comprises a time span of at least five minutes.

10. The method of claim 1, wherein said step of translating continues until reaching a total energy output of at least 500 joules.

11. The method of claim 1, wherein said step of translating continues until reaching a total energy output in the range from 500 joules to 6000 joules.

12. The method of claim 11, wherein said step of translating continues until reaching a total energy output in the range from 2000 joules to 4000 joules.

13. The method of claim 1, wherein said step of providing a probe capable of emitting energy from a bulbous distal end of said probe in a three dimensional field is further defined as said three dimensional field being 360 degrees.

14. The method of claim 1, wherein said step of providing a probe capable of emitting energy from a bulbous distal end of said probe in a three dimensional field is further defined as said three dimensional field being between 270 and 360 degrees.

15. The method of claim 1, wherein said step of providing a probe capable of emitting energy from a bulbous distal end of said probe in a three dimensional field is further defined as said three dimensional field being between 180 and 360 degrees.

16. The method of claim 1, wherein said step of providing a probe capable of emitting energy from a bulbous distal end of said probe in a three dimensional field is further defined as said three dimensional field being between 90 and 360 degrees.

* * * * *